United States Patent [19]

Mech et al.

[11] Patent Number: 4,652,261
[45] Date of Patent: Mar. 24, 1987

[54] DRUG-INJECTION ANIMAL CAPTURE COLLAR

[75] Inventors: L. David Mech, Minneapolis; Richard C. Chapman, Brooklyn Park, both of Minn.; William W. Cochran, Champagne, Ill.

[73] Assignee: Regents of the University of Minnesota, Minneapolis, Minn.

[21] Appl. No.: 623,389

[22] Filed: Jun. 22, 1984

[51] Int. Cl.$^4$ .............................................. A61D 7/00
[52] U.S. Cl. ..................................... 604/130; 604/69; 119/106; 119/151
[58] Field of Search ................. 128/DIG. 12, 13, 305; 604/69, 67, 27, 30, 130; 325/66, 118; 119/106, 107, 29, 151

[56] References Cited

U.S. PATENT DOCUMENTS

| | | | |
|---|---|---|---|
| 1,349,665 | 8/1920 | Duncombe | 119/106 |
| 3,043,303 | 6/1962 | Still | 604/66 |
| 4,180,013 | 12/1979 | Smith | 119/29 |
| 4,314,560 | 2/1982 | Helfgoff et al. | 128/305 |
| 4,335,682 | 6/1982 | Gonda et al. | 119/29 |
| 4,395,259 | 7/1983 | Prestele et al. | 128/DIG. 13 |
| 4,474,575 | 10/1984 | Eckenhoff | 604/131 |

OTHER PUBLICATIONS

Trak Microwave Corporation, (Advertisement from) *Outdoor Life*, Oct. 1964.
Van Citters, R. L. et al., *The Baboon In Medical Research II*, 1967, H. Vastbors, Ed., Univ. of Texas Press Austin pp. 473–492 (Article entitled: *Radio Telementry of Blood Flow and Blood Pressure in Feral Baboons: A Preliminary Report*).
Van Citters, R. L. & D. L. Franklin, Radio Telemetry Techniques for Study of Cardiovascular Dynamics In Ambulatory Primates, Annals NY Acd. Sci. 162:137–155.
Platt, Earl A., *Dual Stage Piston Actuator*, 1979 Defense Systems Division Honeywell, Inc. Hopkins MN.

*Primary Examiner*—Dalton L. Truluck
*Assistant Examiner*—Karen L. Kaechele
*Attorney, Agent, or Firm*—Kinney & Lange

[57] ABSTRACT

A drug-injection animal collar includes electrically operated drug injection darts or syringes that are controlled by control circuitry mounted on the collar which may be preset and self-timed and actuated, or may be remotely actuated by radio signals. The collar is placed on the neck of an animal and upon receipt of a signal, a suitable drug is injected into the neck muscles of the animal. The collar and its method of operation allow regular recapture of individual animals at will for research purposes. The collar and darts may be reconditioned and then reused. The power for operation is also contained in the control package carried by the collar.

23 Claims, 4 Drawing Figures

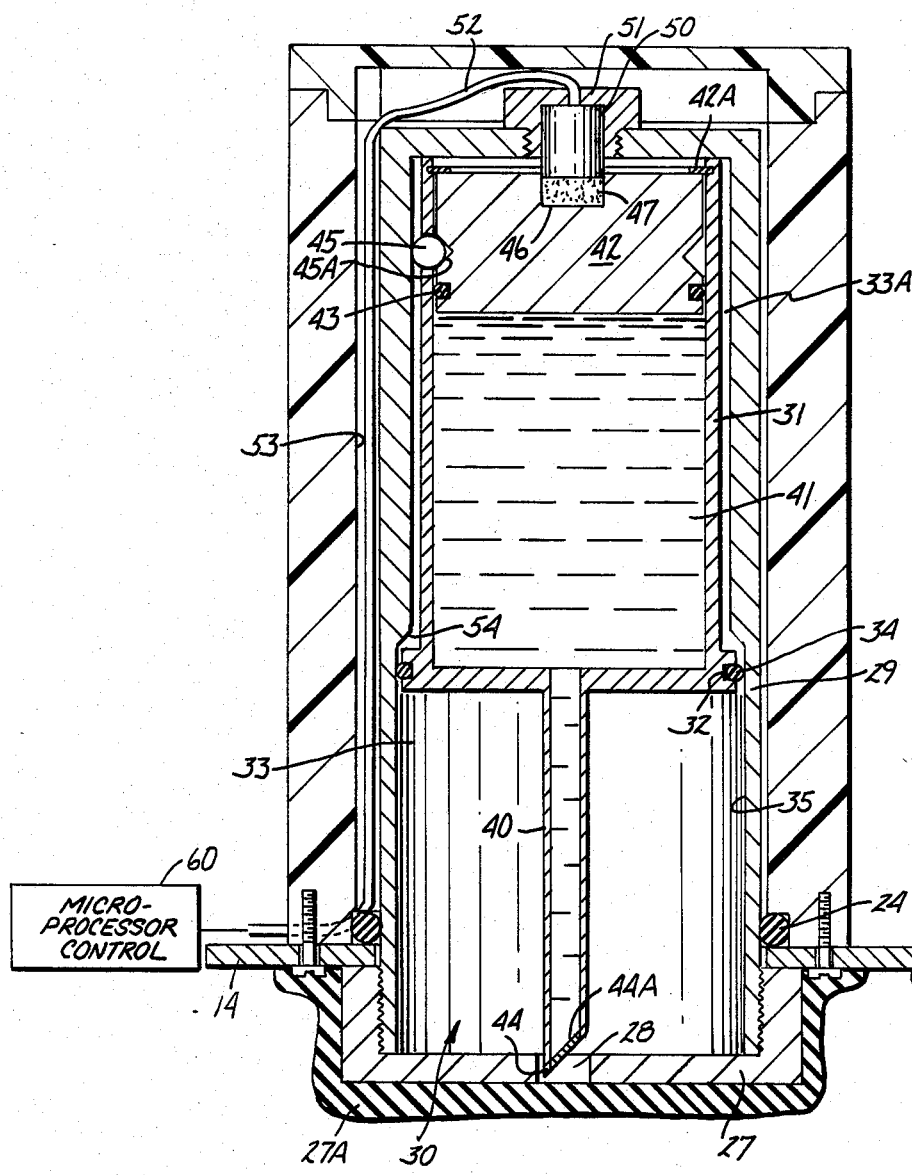
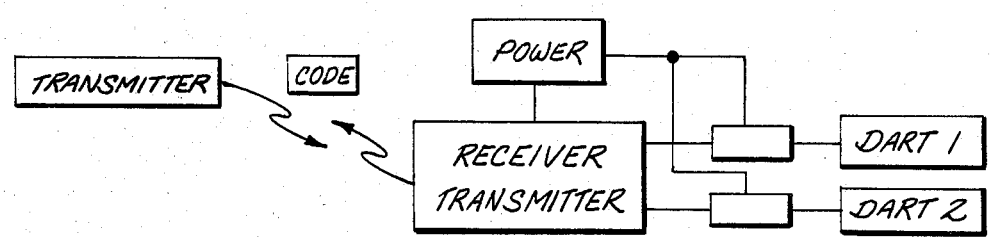
Fig. 2
Fig. 3

DRUG-INJECTION ANIMAL CAPTURE COLLAR

BACKGROUND OF THE INVENTION

1. Field of the Invention.

The present invention relates to a capture collar placed on the neck of an animal that mounts darts for injection of drugs for immobilizing the animal in response to signals.

2. Prior Art

Radio tracking further studies of wildlife ecology by allowing investigators to find and identify individual animals at will. Radio tracking using transmitters attached to the animal has been done extensively in wild animal studies but difficulty is encountered in recapture. The result is a one-time examination of the study animal's nutritional and physiological condition followed by surveillance and a history of the creature's survival and behavioral and ecological interactions. Simultaneously blood sampling, hair sampling, and other physiological testing provide insight into the physiological state and nutritional condition of wild animals.

Radio-tracking and physiological testing are readily combined because to attach a radio-transmitter collar to an animal, the investigator must capture the creature and the researcher can then also conduct physiological tests.

However, because an animal's physiology and nutritional condition changes constantly, samples and tests taken only at initial capture, or at infrequent recaptures of study animals, provide an incomplete assessment of the animals condition. In addition, such procedures as the sodium-turnover technique for determining food consumption in carnivores and other procedures require that individuals be recapturable at certain preselected intervals. Thus a method is needed to recapture animals at will.

Mehods used to capture and recapture animals include live-traps, nets, rifles and pistols firing anesthetic darts, drug-laced food stuffs, etc. For the most part, these methods are unpredictable as to when an animal will be captured, and require proximity to the animal and intensive effort, or else constant monitoring. Furthermore, the methods now used are usually totally unreliable in taking any given animal at will.

One method used employed a radio-triggered drug capsule implanted in baboons carrying backpacks (R. L. Van Citters, O. A. Smith, D. L. Franklin, W. S. Kemper, and N. W. Watson, 1967, in *The Baboon In Medical Research II*, H. Vastbors, Ed., University of Texas Press, Austin pp. 473–492; R. L. Van Citters and D. L. Franklin, 1969, *Radio Telemetry Techniques For Study Of Cardiovascular Dynamics In Ambulatory Primates*, Annals N.Y. Acad. Sci. 162: 137-155). A needleless "syringe" was implanted subcutaneously on baboons with wire leads running from it to the electronic unit in the backpack. The "syringe" consisted of a stainless-steel cylinder with a small hole at one end stoppered by silicon rubber. A rubber piston was friction-fitted into the opposite end, and the chamber filed with a tranquilizing agent. A wad of nitrocellulose was placed behind the piston and secured by a model airplane engine glow-plug. When the device was triggered by remote radio transmission the hot glow-plug exploded the nitrocellulose, driving the piston forward, and injecting the tranquilizer subcutaneously.

Shortcomings of the backpack method are that it required an implanted "syringe" with transcutaneous leads to the triggering mechanism within the backpack. This type of design can lead to infection at the site of entrance of the wire leads through the skin, and breakage of the leads upon movement of the backpack. The leads are also subject to breakage and deliberate removal by associate animals. Furthermore, it requires a surgical operation, with attendant difficulties and potential complications, following each capture to remove the spent "syringe" and replacing it with a fresh "syringe". The backpack was not used to recapture individual animals repeatedly. Animals were recaptured primarily to remove the backpack since it contained expensive physiological measuring electronics.

SUMMARY OF THE INVENTION

The present invention relates to frequent recapture at will or at desired time intervals of wild and captive animals. The collar may be used on captive animals if they are difficult to capture by other means or if they are in large enclosures. The capture collar includes an electronic control and power system and its holder, and one or more "dart" or syringe assemblies. The dart assemblies are held in a suitable position on the neck of the animal and are actuated with pyrotechnic squibs to force a needle into the neck muscle of the animal and then to deposit a desired drug into the muscle.

Different types of electronic control systems may be used with the capture collar. Transmitters for locating the animal are used and may have receivers to pick up remotely transmitted triggering signals. Such triggering signals may be codes to change the transmitted signals, and/or to fire the darts.

Other control systems may be microcomputer based. The operation then will depend on the program residing in its memory chip. For example, the normal tracking signal pulse rate presently used is about 60 pulses per minute. The receiver on the collar may be turned on for several milliseconds every second to determine if a code from a remote transmitter is being transmitted to it. The microcomputer may be programmed to transmit status information periodically and to change behavior if conditions warrant. Each collar is programmed to accept a unique frequency-code combination for activation as is known in the art.

Signal encoders to activate the electronic modules can be plugged into microphone jacks of conventional communication radios. The encoders can also be used with handheld commercial aircraft transmitters or with special transmitters manufactured for the purpose. The radio signal used to trigger a capture collar can be as simple or as complicated as needed and a wide range of transmitting and receiving (telemetry) equipment is available commercially to accomplish the purposes. Once the objective of operation is established, transmitters and receivers may be selected to accomplish the purposes, including the broadcast of a single carrier frequency, modulated carrier, pulse interval, pulse width, AM or FM, etc.

Simplified controls are shown, because the programming of signals is primarily a matter of the desires of the biologist or person interested in capturing the animal.

In a preferred form the control includes a microcomputer based timer actuated sequence. The timer and controls are mounted on the collar and may be preset to actuate the darts or syringes at known intervals. A transmitter mounted on the collar may be used for tracking the animals and may be controlled by the microcomputer to provide information as to imminent firing of the darts and information indicating any malfunction.

It is readily apparent that several control systems can work with the capture collar thus greatly increasing its utility under many different conditions. The programmable timer controls may have a set dart firing time thus eliminating the need for a receiver on the collar and any remote triggering transmitter. Models used for captive animals, (for example in zoos where the animals are in compounds) may not require the location transmitter.

The preferred dart assemblies comprise a barrel enclosing an electrically triggered explosive (squib) that propels a two stage piston-dart with an attached needle. The two stage piston insures that the drug is not expelled until the dart's needle has nearly extruded its full length. Any suitable explosive or ignitable substance could be used in liquid, powder, pellet, or solid form. The expanding gases from the explosion or burning of the charge propel the dart downward forcing the needle into the neck muscle of the animal and then the second stage piston moves to force drugs contained in the dart to be deposited in the muscle. Single stage darts may be used, and the drug may be in powdered, solid or liquid form, as desired. Liquid form is disclosed.

Other potential dart driving methods include solenoids, or expansion of $CO_2$ or other compressed gases, expansion of butane or other volatile substances, or spring-loaded darts that release their contents upon receiving a signal that releases the mechanism.

Various combinations of the following anesthetic drugs have been used in the darts: phencyclidine hydrochloride; promazine hydrochloride, xylazine, ketamine hydrochloride, and etorphine. Additionally, propylene glycol has been added to these drugs to prevent freezing of the drugs during cold weather use of the collar. Other drugs or combinations of drugs are visible and are dictated by the needs of the species in question.

The electronic system and power supply carrier and dart holders have been of aluminum or synthetic material such as "Delrin", Boltron, nylon or acrylic plastics. The dart holders or housings provide water-proofing and mechanical protection (from chewing for example). The size and material used are generally dictated by the type of animal and environmental conditions. Machine belting and nylon belting and webbing have been used as collar materials. The collar is placed snugly around the animal's neck and closed to secure it in place. The power pack and electronic controls provide counterweight to keep the collar properly positioned. Also, a suitable silicon based sealant is used to encapsulate the dart assemblies and housings after assembly to a collar to insure weatherproofing. The housing for the power pack and controls is also sealed to prevent weather damage.

The collar of the present invention has several advantages over the prior art. It is easier to use, lighter, cheaper, and has modern, high-reliability electronic circuits. It does not require surgical operation for use, and it does not have an infection risk.

The collar allows regular recapture of individual animals which otherwise would not be possible. The use will allow laboratory-quality physiological studies of elusive wild animals which heretofore have not been undertaken because of the extreme difficulty of recapturing animals predictably.

BRIEF DESCRIPTION OF THE DRAWINGS

FIG. 2 is a vertical sectional view taken as on line 2—2 in FIG. 1;

FIG. 3 is a schematic representation of circuitry utilized for a type of remote control used with the present invention.

DETAILED DESCRIPTION OF THE PREFERRED EMBODIMENTS

Figure 1:
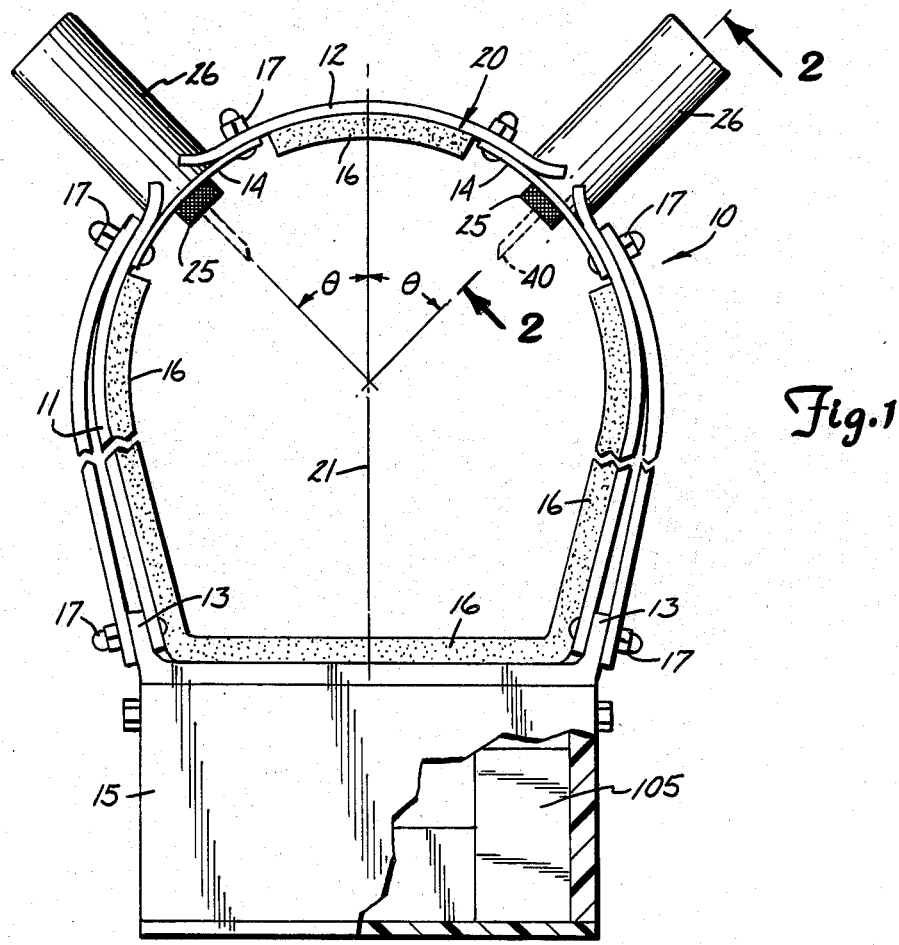
FIG. 1 is a front elevational view of an animal capture collar made according to the present invention.

An animal capture collar indicated generally at 10 comprises layers of belting 11, which form side collar sections and an upper belting section 12. These sections are connected to thin metal or plastic support sections 14, which, as will be explained are used to support dart assemblies. The lower end of the collar is closed by attaching collar sections 11 to ears 13 which are an integral part of a battery and control housing or case 15. As shown the inner surfaces of the collar may be covered with suitable foam or padding 16. The padding can be adhesively fastened in place and will further enhance positional stability, as well as accommodating changes in the size of the neck. The battery and control case 15 provides a weight, which tends to keep the collar properly oriented. The collar sections and control case may be held together with any suitable fasteners. As shown, bolts 17 are used.

The upper end of the collar 10 is indicated at 20, and is rounded to fit comfortably over an animal's neck. At suitable angles indicated at $\ominus$ relative to a fore and aft vertical bisecting plane 21 thereto, there are a pair of dart-hypodermic syringe and needle assemblies 25 (called dart assemblies). Each of these dart assemblies 25 has a central axis. As shown the dart assemblies are inserted into outer dart assembly housings 26, which are attached with screws and a silicone based adhesive to the metal sections 14. The outer housings 26 have open ends and dart assemblies 25 are as shown frictionally held in place with "O" rings 24 that are compressed as the dart assemblies are installed with their ends on the inside of the collar 10. The dart assemblies may be held in place with a silicone based adhesive.

A typical dart assembly 25 is shown in FIG. 2, and includes a dart housing 29 forming an interior chamber 30 and having a cap 27 thereon with a center opening 28 through which a drug injection needle can be propelled. The outer housing may form the dart housing if desired, so only one housing would be used. The chamber 30 has two chamber portions 33 and 33A which mounts a first piston comprising a container 31. The container 31 has an annular piston flange 32 that fits within a chamber portion 33 at the lower or outlet end of the housing 29. A suitable O ring 34 seals piston flange 32 with respect to the inner surface 35 of the chamber portion 33. The container 31 and flange 32 form a primary piston. The container 31 slides into chamber portion 33A and has a hypodermic needle fixed thereto at one end. The needle 40 opens to an interior chamber 41 of the container 31. Hypodermic needle 40 is, in the initial position retracted within the end cap 27.

The interior chamber 41 of container 31 is cylindrical, and a secondary piston member 42 is slidably mounted therein. The remote end of chamber 41, (the end farthest from needle 40) is open to permit piston 42 to be inserted. The secondary piston member 42 as shown is retracted toward the open end of the chamber 41, and has a suitable O ring or seal 43 around its periphery to form the piston seal. A snap ring 42A provides a stop to prevent the piston 42 from rebounding out of the chamber before it operates.

The secondary piston 42 is detented in the retracted position with one or more suitable detent balls 45 that fit into a groove 45A on the outside of the secondary piston. Ball 45 protrudes through a provided detent opening in the wall of the container 31 and rides against the inner surface of the chamber section 33A. When the piston 42 and container 31 are both retracted, as shown, the secondary piston cannot move axially relative to the container.

At the upper or remote end of the secondary piston 42 there is a solid propellant chamber 46 in which a suitable pyrotechnic material 47 of known consistency is placed. A "squib" or detonator indicated generally at 50 is positioned adjacent the pyrotechnic powder and held in place with a removable cap 51 which forms a squib holder. A "squib" is a device that will detonate or ignite the pyrotechnic powder and cause burning, or in other words, a controlled explosion, to provide a gas pressure within the chamber 30 to act on both the container-piston 31 (through secondary piston 42) and flange 32. The cap 51 is on the outside of the housing 29 to hold the squib in place against the propellant 47 when the piston 42 is retracted. The squib may be glued in place in the cap 51. Suitable electric leads 52,52 from the squib provide for detonation. The leads 52,52 extend through a slot 53 in the outer housing 26. The leads may be held in place with a suitable sealant. The leads also extend along the collar sides to the control housing 15.

The lower end of the hypodermic needle 40 has a sharpened point portion indicated generally at 44 that is closed with a suitable plug 44A, such as a wax or an elastomer, to prevent the drug in the chamber 41 from escaping until it is forced out.

Each of the dart assemblies 25 is preferably controlled by microcomputer based control circuitry indicated at 60, and upon detonation of either one of the darts, the controlled squib will fire the pyrotechnic material 47 which will result in gas pressures being formed in the upper end of the chamber 30, above secondary piston 42. The pressure will act on the upper surface of the piston 42, and on the upper surface of flange 32, above seal 34. Because the detent ball 45 will hold the secondary piston, the container 31 and the needle 40 will be forced outwardly through the provided opening 28, and into the neck of an animal wearing the collar. As the container 31 moves toward the cap 27 it will move to a position where the hypodermic needle is inserted a desired amount into the neck muscles of an animal. The container 31 will then have moved to a position where the ball 45 will align with release shoulder 54 that forms the junction between chamber sections 33 and 33A and the ball will be permitted to move radially outwardly, clearing the annular groove 45A in the piston 42. The pressure in the upper chamber section 33A then will act to force the secondary piston to move within the interior chamber 41 of container 31. The secondary piston 42 will force the drug out through the pointed end 42 of the hypodermic needle 40, forcing the plug 44A out of the way to inject the drug from the container chamber 41 into the neck muscle into which the hypodermic needle has been inserted. This will initiate the drug action and will cause the animal to be capturable.

The remote radio controls utilized for remote actuation of the darts can be of any desired form. Locating transmitters, which are well known, may be used to provide a signal to a remote receiver indicating the location of the animal. A remote transmitter would provide a coded signal (much like existing aircraft transmitters, but with different codes) that would, at a particular time fire one or both of the darts in the collar to immobilize the animal.

As shown in FIG. 3, a simplified schematic representation of a typical, simple remote transmitter arrangement is shown. The housing 15 would contain a power supply 70, and a receiver/transmitter 71 which would include the suitable code receivers, in a conventional manner. When the receiver receives a suitable preselected signal it provides an output on a line 72 through a control 73 from the power supply 70 to fire dart number one, which is indicated at 74, through leads 52. Dart 74 can be either on the right or left hand side of the collar. The firing as shown comprises the actuation of the squib, but for other types of darts other actuators for injecting the drug may be used.

The signal to the receiver/transmitter 71 is provided from a remote transmitter indicated at 75 which could be on an aircraft, hand held or the like, and which would provide a coded signal to the receiver/transmitter 71 to fire the dart. The antenna for receiver/transmitter 71 comprises the leads 52, which serve double duty.

If the animal was not then captured by ground personnel, or if there was an indication, either visually from aircraft observance, or from indication of bodily functions that might be monitored by the receiver/transmitter 71, a second coded signal would be fired to the receiver/transmitter 71 to provide a signal along a line 76 through a switch 77 to provide power to the squib on dart number two indicated at 78. When both darts have been fired, the animal would normally be sufficiently drugged to permit capture, or at least to permit approaching within a range wherein a separate dart gun could be used for immobilizing the animal for scientific research.

Figure 4:
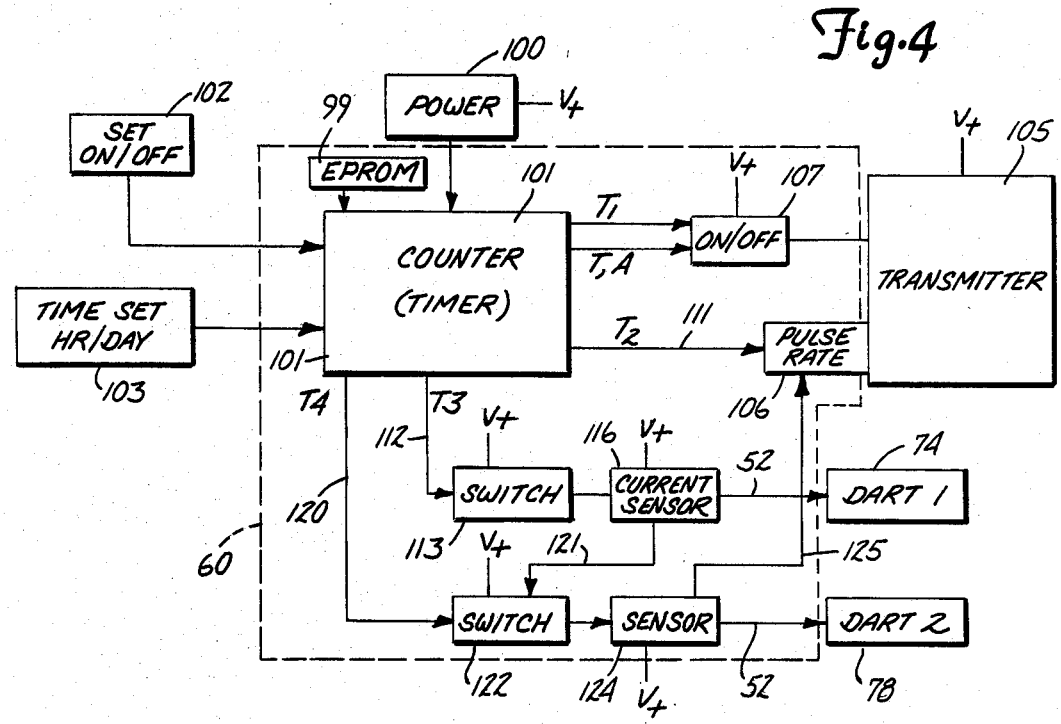
FIG. 4 is a schematic representation of a modified form of the control system of the present invention illustrating essentially a self-contained, self-powered timer arrangement included on a microcomputer chip or logic chip.

A more preferred embodiment, with the advent of solid state microprocessors of low power consumption, and with the ability to be programmed in a wide variety of ways, is shown schematically in FIG. 4. All of the components on the microcomputer based control 60 could be on one or more chips of a microprocessor having a sufficient memory to provide the necessary functions. For example an RCA CDP1802D 301R microprocessor will fulfill the necessary requirements for use. Also, a one chip computer such as an MC1468705G2 may be used. Custom designed chips for accomplishing desired results also are within the skill of the art. The microprocesser is housed in a simple small dual in-line package. An EPROM 99 included in the instant package provides the control program and memory for the microprocessor based control 60.

Essentially, a power supply, again a battery of suitable design, indicated at 100 would be provided to provide power to the various components. The microprocessor includes a counter 101 which has a number of individual counter sections, and dividers to comprise a timer that provides a number of output signals at set times in a conventional way. As part of the controls, a "set" and on/off control 102 is used to set the timer 101 at desired intervals, and to power it. In addition controls 103 can be used for setting the elapsed time for each of the individual outputs. The hour and day of the elapsed time for providing each of the time outputs is individually set, again in a conventional manner. Normally, the counter would provide beeps indicating a particular elapsed time period and then by setting the control after the desired number of beeps have been heard the time signals at the different time intervals can be controlled. Alternately, the periods are preprogrammed into the EPROM 99. The counters are solid state counters which count down from the time of setting and when the counting down is completed a time signal is provided. The timer may be reset by the program in EPROM 99 if desired.

In this form of the invention, a transmitter providing a pulse signal is indicated generally at 105 is part of the instrumentation package, and it is made so that it can have a pulse rate control 106. The pulse rate control normally is a divider that would divide the set transmitted pulse rate by a selected integer.

An on/off solid state switch indicated at 107 would be used for turning on or off the transmitter as desired. The transmitter is powered from the power supply 100 in a conventional way. At a time $T_1$ from timer 101, the transmitter could be turned on, and at a time $T_{14}$ the transmitter could be turned on through the switch 107. These times may be cycled as desired. The transmitter could be turned off to conserve power if a long period of time was to elapse between the initial placing of the collar on the animal and the first firing. In this way, the transmitter could be turned on and off for a short period of time each day, or each hour, so that persons observing the animal would be able to keep track with a remote receiver.

At a time $T_2$ indicated generally along a line 111 the pulse rate control 106 could be made to alter the transmitter pulse rate to aid in identifying the particular animal that is being tracked, or for other reasons of simplification of tracking.

In one specific operational example, at time $T_2$, which was selected to be fifteen minutes before the firing of the first dart, the pulse rate was changed to be two pulses per second, but unevenly spaced, as a warning signal. That is two quick pulses were provided each second, with a longer lapse between the sets of two pulses. This signal was a warning and would continue that way until a dart was fired.

In the form shown in FIG. 4 at time $T_3$, which is the dart firing time preprogrammed into the timer or counter 101, a signal would appear along a line 112 to a solid state switch 113 that provides an electrical signal to the squib of one of the darts, for example, dart one, indicated at 74, to fire the dart. The lead 52 leading to the squib has an integrity check current sensor 116 or similar conventional sensor for checking for an open circuit. Under normal circumstances, after dart one has fired, at a time $T_4$, which would be an interval after $T_3$, a signal would appear along a line 120 to switch 122 to fire dart two. For example, in actual cases intervals of 30 minutes and 60 minutes between times $T_3$ and $T_4$ have been used. If the first dart 74 immobilizes the animal sufficiently to permit capture during that interval, before time $T_4$, then the second switch 122 can be manually disabled so that the second dart 78 would not fire at all.

Sensor 116 is part of the microcomputer control 60 and if dart one developed an open circuit after firing or there was another malfunction detected, a signal is provided along a line 121 to the switch 122 that controls power to dart 78 to immediately fire that dart. If a sensor indicated at 124 indicates that there is an open circuit in the line to dart 78 as well, a signal is provided along a line 125 to the pulse rate control 106 to change the pulse rate of the transmitter (lower it) to provide an indication that there are open circuits to the darts and to conserve power to increase the time available for recapture. The microprocessor memory and EPROM 99 program will provide for these control functions.

Using two lithium C size cells in series for power supply 100, the transmitter 105, transmitting 60 pulses per minute, twenty four hours a day has a theoretical life of seven months under normal temperature conditions. By programming the transmitter to be switched on and off through switch 107 so that it was on from 8:00 A.M. to 8:00 P.M. each day and off for the other half of the day, the battery life can be increased to about twelve months.

The microcomputer components, the transmitter, and the batteries are housed in the housing 15. The housing is hermetically sealed, but may be opened to change batteries or to change the program of EPROM 99 to alter operation of the microcomputer. The entire collar weighs about 680 grams, although it could be made to weigh up to 250 grams less if smaller batteries and/or smaller darts are used. A one chip computer version (MC1468705G2) may weigh as little as 120 grams. Then, the firing interval can be easily changed with the existing microcomputer technology, and the ability to set a schedule of firing of the darts provides for ability to closely monitor the animal activity, and its physiological state.

The microcomputer also can be radio triggered merely by the addition of a miniature radio signal receiver, such as that shown schematically in FIG. 3, and with proper coding of signals the transmitter set up can be used to check circuitry and provide a readout on the status of the components in a normal telemetry operation.

The target animal is captured by conventional means and anesthetizing drugs are loaded into each dart container chamber and assembled on the collar. A layer of sealant may be used to weatherproof the dart housing as shown at 27A in FIG. 2.

The microcomputer is programmed to provide the desired functions including the timer signals. The timer is set to run for time of recapture by simply throwing a switch after the time sequences have been set. In the case of a transmitter/receiver control the power is turned on and the components placed in the housing 15. The control housing is sealed and the lead wires to the squib are attached. The wires also can be sealed with a suitable sealant.

The collar is placed around the animal's neck and the animal is released. The transmitted signal is monitored as often as necessary for location data or accumulated activity data of the animal.

For on-command operation, as shown in FIG. 3, a triggering signal is sent to the collar by the ground crew or from an operator in an aircraft when the animal is to be recaptured. For the self-contained timer operation as shown in FIG. 4, before the preprogrammed time and day of recapture, the animal is located by conventional tracking methods and a ground crew moves near the animal. The signal is monitored and an appropriate period is allowed to elapse after dart one fires before the ground crew moves to the animal. If the first dart was unsuccessful in immobilizing the animal, the second dart is fired after a known interval (at T₄).

When the animal is examined, the collar is removed and placed in reset mode by opening the case and throwing a switch, which will also disable the second dart (FIG. 4 version). Following appropriate processing of the animal for physiological or other types of data, a new or refurbished collar is placed on the animal and the animal is released, and monitored until the next recapture period arrives. The collar is refurbished by replacing spent dart assemblies, batteries, damaged components and the like as needed.

As shown, each dart contains a desired volume of the drug selected to immobilize the animal on which the collar is used. The collar has been used on deer, wolves, black bear, and captive cougars and tigers with satisfactory results.

The collar is a preferred support because it is easily put on, is not easily rubbed off or chewed off and can be sized by using different length collar sections 12 shown in FIG. 1.

Although the present invention has been described with reference to preferred embodiments, workers skilled in the art will recognize that changes may be made in form and detail without departing from the spirit and scope of the invention.

What is claimed is:

1. An animal capture collar comprising a collar of a size to encircle the neck of an animal to be captured, a power and control pack mounted at one end of said collar to cause the collar to move to position with the power and control pack toward the lower portion of the animal neck;
   a pair of needle injection dart assemblies mounted on said collar adjacent an opposite end thereof from the power and control pack, said dart assemblies being fixed to said collar and having end portions on the interior of said collar and at substantially equal angles on opposite sides of a vertical bisecting plane extending in direction of the length of the animal's neck, said dart assemblies having end portions that are adjacent the neck of an animal on which the collar is mounted; and
   explosive pyrotechnic means adapted to actuate said needle dart assemblies to first inject the needle into the neck of such animal and subsequently force a drug through said needle into the tissue of an animal on which the collar is mounted.

2. The apparatus as specified in claim 1 wherein said power and control pack includes a transmitter providing a signal capable of being received to identify location of the transmitter.

3. The apparatus as specified in claim 1 wherein said dart assemblies each include a pyrotechnic device capable of being initiated upon receipt of an electrical detonation signal, and timer means contained in the power and control pack to actuate at least one of the dart assemblies at a given time period after initiation of the timer means.

4. The apparatus as specified in claim 3 wherein said timer means includes means to provide a second signal prior to the first time signal that alters the state of the transmitter to provide transmission of a different signal for a set time prior to the detonation of the first dart assembly.

5. The apparatus as specified in claim 4 and means sensitive to determining firing of said one dart assembly, said means sensitive responding to a signal indicating a condition showing the first dart did not fire, initiating the second dart assembly mounted on said collar substantially simultaneously to determination that the first dart assembly has a condition indicating a lack of operation.

6. The appartus as specified in claim 4 wherein said timer means provides an additional time signal operably connected to said second dart assembly to detonate said second dart assembly a length of time subsequent to the detonation of the first dart assembly.

7. The apparatus as specified in claim 4 wherein said timer means provides separate time signals to control said transmitter, switch means responsive to the separate time signals to control power to said transmitter, said separate time signals controlling said switch means to turn off said transmitter for preselected intervals of time after initiation.

8. The apparatus as specified in claim 1 wherein said dart assembly comprises an outer housing, a dart cartridge mounted in said housing, said cartridge including a needle portion, and container means forming a container chamber, said container fitting within said housing, and said needle being carried by said container at one end thereof and mountable within said housing adjacent an end thereof close to the collar, said container having a sealing means to seal it relative to the housing to form a first slidable piston, said container being sealingly fitted in said housing at locations spaced from said end, a second piston mounted in said container and movable from a first position to a second position, said first position being remote from said needle and said second position being adjacent said needle;
   detent means to retain said second piston in said first remote position, said container chamber and said needle defining a receptacle for holding a desired liquid drug; and
   means to generate a propellant gas at an end of said housing opposite from the end adjacent the collar, electrical signal receiving means for initiating operation of said propellant gas, said gas generating a force to move said container in the housing and force the needle outwardly of said housing by providing a pressure between the sealing means between said container and said housing until said container is moved to an actuated position with the needle protruding from said housing, means to permit said detent means to release when the container reaches its actuated position, thereby permitting said second piston to move within said container chamber, said propellant gas thereafter forcing said second piston in direction toward said needle to expel the drug held in the container chamber out through the needle, until said piston reaches its second position.

9. An animal capture system for permitting the immobilization of animals at a selected time, including:
   a collar adapted to fit around the neck of an animal with at least a first portion of the collar substantially contiguous to skin of an animal on the upper sides of the neck and resting on muscle tissue;
   a remotely actuable drug injection dart assembly mounted on the first portion of said collar and having a needle portion with a needle axis positioned so that upon actuation the needle will penetrate the skin of an animal wearing the collar, said dart assembly including means causing a suitable material to be injected into the neck muscle tissue of such animal the needle axis lying substantially on the plane of the collar;

control means for actuating said dart assembly upon the presence of a signal, said control means including a self contained power supply for actuating said dart assembly; and a housing mounted on said collar to enclose the collar at a side thereof opposite from the first portion, said control means being mounted within said housing to provide a weight ballast to tend to keep the collar oriented in a proper position on the neck of an animal on which the collar is mounted and to facilitate retention of the first portion of the collar and the dart assembly against the neck of such animal, the needle axis also being at an incline with respect to a diametral plane perpendicular to the collar plane and substantially bisecting the control housing.

10. The apparatus as specified in claim 9 wherein said control means comprises a self contained timer capable of being preset at the time the support is placed on such an animal, and including counter means to control actuation of the dart assembly after a predetermined elapsed time.

11. The apparatus as specified in claim 9 wherein there are a pair of remotely actuable dart assemblies mounted on said collar and means to mount said dart assemblies to position said dart assemblies, respectively, adjacent the first portion of the collar and at substantially equal and opposite angles with respect to the diametral plane.

12. The apparatus as specified in claim 9 wherein said housing comprises a housing that is hermetically sealed before placing the collar on an animal.

13. A device for permitting immobilization of animals at a preselected time comprising a collar member of size to fit over the neck of an animal, said collar defining a central plane;

a control housing mounted on said collar member and positioned to be at a first side of the collar member when mounted on an animal;

at least one actuable dart assembly mounted on said collar at a location on an opposite side of the collar from the control housing and having a needle that will penetrate the skin and muscle tissue of an animal, and subsequently cause injection of a preselected material into the muscle tissue of such animal in response to an electrical signal;

microcomputer timer means mounted in said control housing;

power means mounted in said housing for powering said microcomputer timer means, the components in the control housing and the housing providing a weight ballast to facilitate friction retention of the dart against the neck of the animal with the control housing tending to move to position under the neck of an animal on which the1 collar is mounted; and means mounted on said collar operable by said timer means for causing an electrical signal to be provided to actuate said dart assembly.

14. The apparatus as specified in claim 13 wherein the dart assembly is mounted by mounting means comprising a dart assembly housing mounted on said collar, said dart assembly housing having an interior chamber, said dart assembly having an outer dart housing of size to fit within said chamber, and an annular seal mounted at an end of said dart assembly housing adjacent said collar comprising a resilient ring frictionally engaging the outer surface of said dart housing when the dart housing is inserted into said chamber to hold said dart housing in position and seal the chamber from the exterior.

15. The apparatus as specified in claim 14 and a coating of an elastomeric sealant material surrounding the outer end of said dart assembly housing to seal the interior chamber and said dart housing with respect to said collar.

16. The apparatus as specified in claim 13 wherein said control means further includes a locating transmitter member mounted in said control housing for providing a transmitted signal for tracking purposes.

17. The apparatus as specified in claim 7 wherein there are a pair of dart assemblies mounted on said collar at substantially equal and opposite positions with respect to a generally diametral plane of the collar passing through the effective center of mass of the control housing, the dart assemblies both being generally on an opposite side of the collar from the control housing.

18. The apparatus as specified in claim 17 wherein said collar member is made up of a plurality of collar sections, including a section for mounting the control housing at the lower portion thereof, and a removable section at the upper side positioned between the pair of dart assemblies, said removable section being selectable in length to change the effective size of said collar member.

19. The apparatus as specified in claim 11 wherein said dart assemblies include a dart housing comprising a piston chamber having two chamber sections of different diameters, the larger diameter chamber section being adjacent the end of the dart housing that is adjacent the animal wearing the collar;

a two stage piston mounted in said dart housing, including a first sealing ring comprising a first piston sealingly mounted for movement in said larger diameter chamber, a container mounted on said sealing ring and extending into the smaller diameter chamber of said dart housing, the container having an interior chamber, the needle being attached to the container, a second piston member having a second chamber defined therein open to an end facing in opposite direction from the needle mounted in said container chamber, detent means to hold said second piston at a remote end of said container chamber with respect to the collar until the sealing ring and container have moved toward the collar to position wherein said detent means releases and permits said second piston to move in the container chamber toward the collar and push material in the container chamber outwardly through the needle; and means for providing a propelling force to move the first and second pistons toward the collar.

20. The apparatus of claim 19 wherein the means for providing a propelling force comprises a pyrotechnic device mounted in said second chamber of said second piston for providing gas under pressure to act against said first and second pistons upon receipt of said electrical signal, stop means at the remote end of said container chamber to prevent said second piston from moving outwardly from the container chamber.

21. A method of obtaining information relating to animals comprising the steps of providing a collar on the neck of an animal;

providing a pair of controllable dart assemblies on said collar positioned completely to the exterior of the skin on portions of the collar normally positioned near the top of the neck of the animal;

mounting a control package including a microprocessor and power supply on said collar, said control package being opposite the dart assemblies and providing weight to tend to keep the dart assemblies near the upper portion of the neck of the animal;

providing a timer mounted on said collar as part of said control package, and setting the timer to provide the desired signals at desired intervals from the time of placing the support on such animal; and sequentially triggering and firing said dart assemblies upon providing desired signals from the control package to immobilize the animal.

22. The method of claim 21 including the further step of tracking the animal by means of a transmitter located on said support.

23. The method of claim 21 including the step of triggering and firing a first dart assembly in response to a signal, and sensing the circuit of the dart assembly so triggered to determine if there is an abnormality, and immediately triggering and firing the second dart assembly in response to the sensing of an abnormality.

* * * * *